(12) United States Patent
Alarcon et al.

(10) Patent No.: US 9,068,565 B2
(45) Date of Patent: Jun. 30, 2015

(54) CONTAINER AND METHOD FOR STORING A PHARMACEUTICAL AGENT

(75) Inventors: Javier Alarcon, Durham, NC (US);
William Riggsbee, Cary, NC (US);
Joshua Horvath, Sparta, NJ (US);
Dinesh Kommireddy, Derry, NH (US);
Ron J. Pettis, Cary, NC (US)

(73) Assignee: BECTON, DICKINSON AND COMPANY, Franklin Lakes, NJ (US)

( * ) Notice: Subject to any disclaimer, the term of this patent is extended or adjusted under 35 U.S.C. 154(b) by 5 days.

(21) Appl. No.: 13/463,509

(22) Filed: May 3, 2012

(65) Prior Publication Data
US 2013/0296235 A1  Nov. 7, 2013

(51) Int. Cl.
| | |
|---|---|
| A61K 9/14 | (2006.01) |
| F04B 43/00 | (2006.01) |
| A61J 1/06 | (2006.01) |
| F04B 43/08 | (2006.01) |
| B32B 27/18 | (2006.01) |
| B32B 27/32 | (2006.01) |
| B32B 1/08 | (2006.01) |
| A61M 5/31 | (2006.01) |
| A61M 5/14 | (2006.01) |

(Continued)

(52) U.S. Cl.
CPC .............. *F04B 43/0072* (2013.01); *A61J 1/062* (2013.01); *A61J 1/1406* (2013.01); *A61J 2001/201* (2013.01); *F05C 2225/00* (2013.01); *F05C 2231/00* (2013.01); *F04B 43/08* (2013.01); *B32B 27/18* (2013.01); *B32B 27/32* (2013.01); *B32B 1/08* (2013.01); *B32B 2439/80* (2013.01); *A61M 5/3129* (2013.01); *A61M 5/31585* (2013.01); *A61M 2005/2407* (2013.01); *A61M 2005/2488* (2013.01); *A61M 5/14* (2013.01)

(58) Field of Classification Search
CPC ................. A61M 5/31585; A61M 2005/2407
See application file for complete search history.

(56) References Cited

U.S. PATENT DOCUMENTS

| | | |
|---|---|---|
| 4,538,531 A | 9/1985 | Wong |
| 4,685,902 A | 8/1987 | Edwards et al. |

(Continued)

FOREIGN PATENT DOCUMENTS

EP  1028141  8/2000

OTHER PUBLICATIONS

Tarr et al (American Journal of Health-System Pharmacy Dec. 1, 1991 vol. 48 No. 12 2631-2634).*

(Continued)

*Primary Examiner* — Benjamin Packard
(74) *Attorney, Agent, or Firm* — Roylance, Abrams, Berdo & Goodman, L.L.P.

(57) ABSTRACT

A container and method for storing a pharmaceutical agent are provided for enhancing the storage time. The storage time of the pharmaceutical agent is improved by reducing the loss of stabilizing agents in the pharmaceutical agent. The storage container is formed from a polyolefin that includes a stabilizing agent in an amount effective to reduce or inhibit the migration of stabilizing agents in the pharmaceutical agent. The polyolefin container is formed with a fatty acid amide such as erucamide for stabilizing insulin that contains m-cresol and/or phenol as stabilizing agents for the insulin. The fatty acid amide incorporated in the container inhibits and/or reduces the rate of migration of the m-cresol and/or phenol into the polyolefin to extend the storage life of the insulin. The container can be a syringe, such as a pre-filled syringe, a storage vial or the flow path of an infusion pump.

30 Claims, 4 Drawing Sheets

(51) Int. Cl.
    *A61J 1/14*    (2006.01)
    *A61J 1/20*    (2006.01)
    *A61M 5/315*   (2006.01)
    *A61M 5/24*    (2006.01)

(56) References Cited

U.S. PATENT DOCUMENTS

| | | | |
|---|---|---|---|
| 5,077,328 A * | 12/1991 | Haruna et al. | ................ 524/100 |
| 5,331,019 A | 7/1994 | Payne et al. | |
| 5,356,948 A | 10/1994 | Payne et al. | |
| 5,945,187 A | 8/1999 | Buch-Rasmussen et al. | |
| 6,443,942 B2 | 9/2002 | Van Antwerp et al. | |
| 7,029,752 B2 | 4/2006 | Hama et al. | |
| 7,250,037 B2 | 7/2007 | Shermer et al. | |
| 7,807,242 B2 | 10/2010 | Soerensen et al. | |
| 2003/0204001 A1 | 10/2003 | Van Gelder et al. | |
| 2004/0228673 A1 | 11/2004 | Kirita et al. | |
| 2006/0134358 A1 | 6/2006 | Madsen et al. | |
| 2011/0190694 A1 | 8/2011 | Lanier et al. | |
| 2012/0046411 A1 | 2/2012 | Kulshrestha et al. | |

OTHER PUBLICATIONS

International Search Report and Written Opinion dated Sep. 13, 2013 in corresponding PCT Application No. PCT/US13/38864.

* cited by examiner

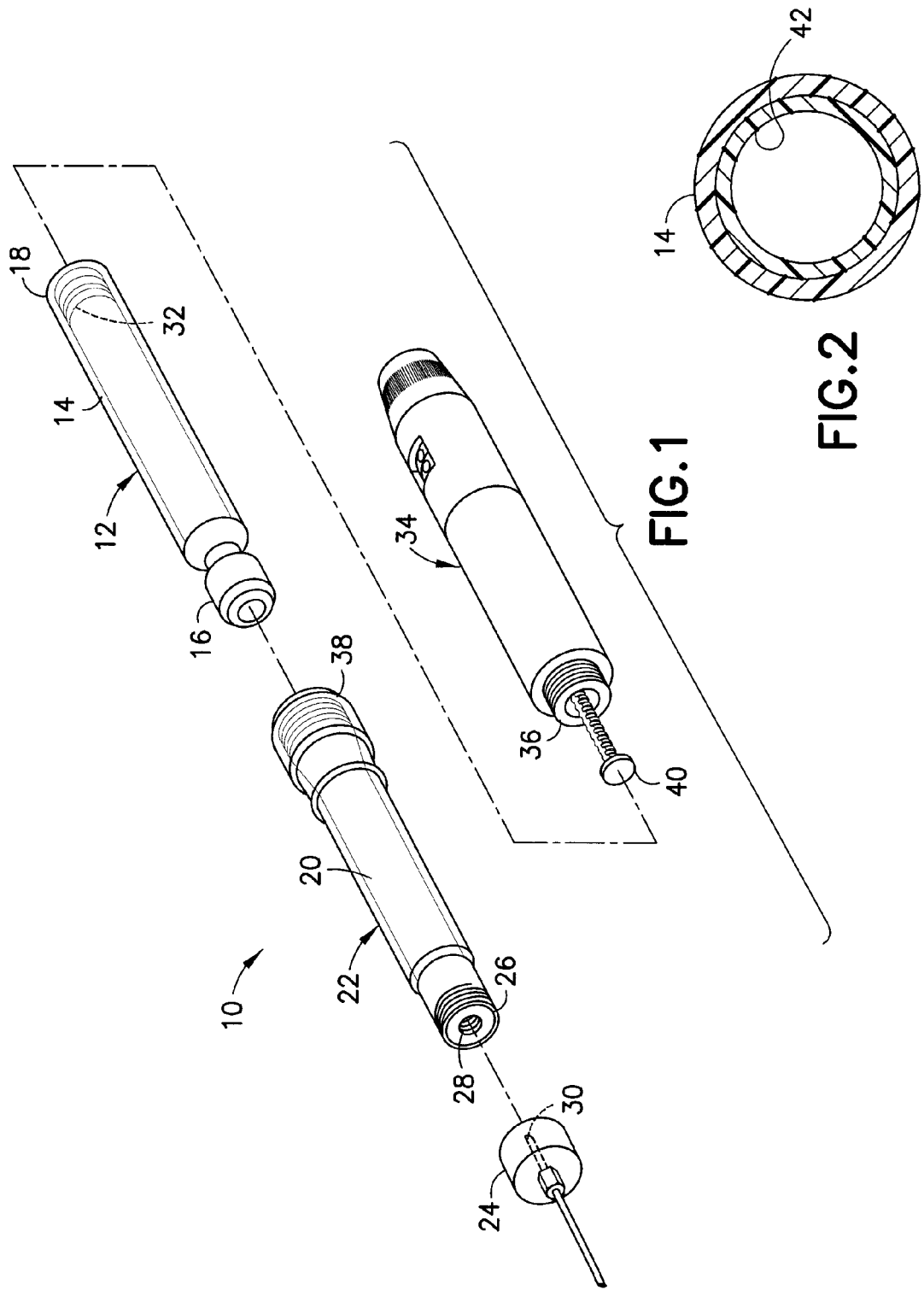

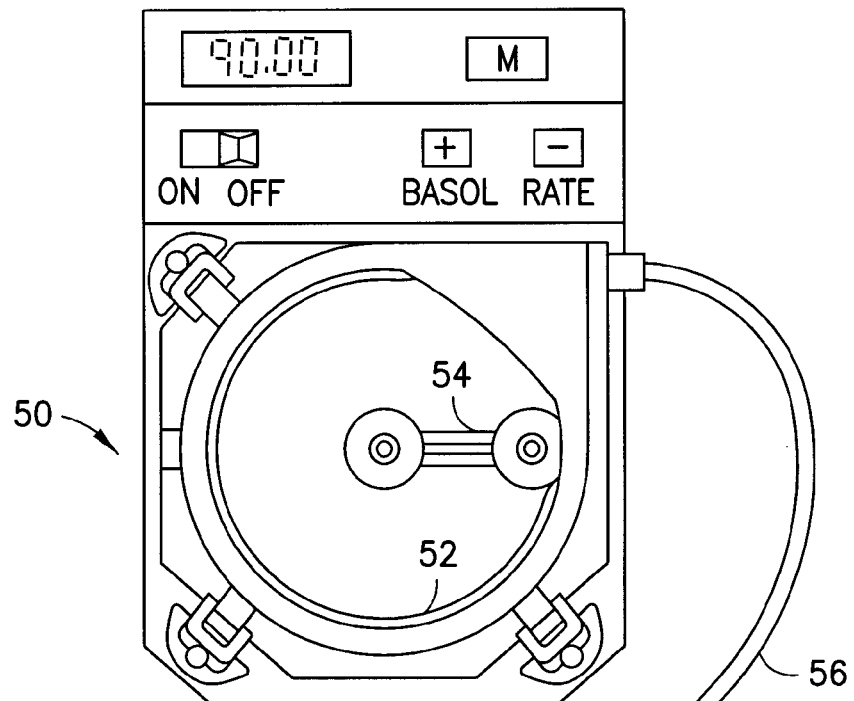
FIG.3
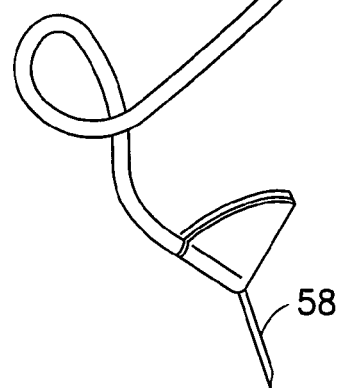
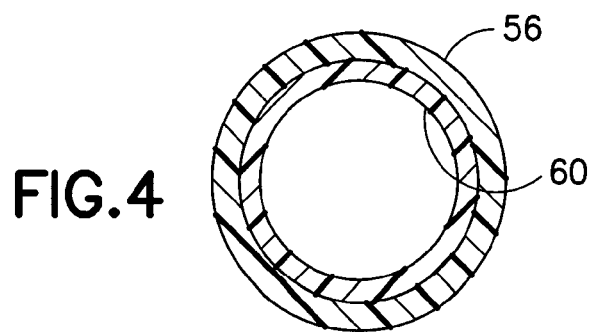
FIG.4

CONTAINER AND METHOD FOR STORING A PHARMACEUTICAL AGENT

FIELD OF THE INVENTION

The present invention is directed to a storage container or storage vessel adapted for extending the storage time for a pharmaceutical agent or liquid medication and to a method for extending the storage life of the pharmaceutical agent or liquid medication. In particular, the invention is directed to a container or vessel and to a method for inhibiting the loss of stabilizing agents in the pharmaceutical agent or liquid medication, thereby extending the life of the pharmaceutical agent or liquid medication.

BACKGROUND OF THE INVENTION

Pharmaceutical agents and medicaments are commonly packaged and stored in storage containers under conditions to provide an extended shelf life. Liquid pharmaceutical agents and medicaments require storage contains that are sufficiently transparent to enable the user to visually inspect the product prior to use. Glass containers are commonly used to provide a non-reactive container to reduce degradation of the product and provide the necessary clarity for visual inspection.

Many pharmaceutical agents and medicaments are unstable or contain additives that diffuse into the wall of some containers which can result in degradation of the product. Glass ampules and containers generally provide a longer shelf life for liquid medications than containers made from polymeric materials. Polymeric containers are desirable from a manufacturing standpoint since they can be easily molded and are lightweight at low cost. Some pharmaceutical agents and medicaments are not suitable for long term storage in containers made from polymeric materials that can react with or adsorb/absorb components from the pharmaceutical agent or medicament.

Many pharmaceutical agents and medicaments require preservatives or stabilizing agents to improve the shelf life. One example is insulin which includes a preservative such as m-cresol, phenol, and/or mixtures thereof. The m-cresol and phenol can diffuse into many polymeric materials that are commonly used to make storage containers. The loss of the preservative from the insulin can result in the rapid degradation of the insulin during storage.

Various methods have been proposed for stabilizing pharmaceutical agents and medicaments for long term storage and producing storage containers and vessels that are able to provide long term storage. One example is disclosed in U.S. Pat. No. 5,945,187 to Buch-Rasmussen et al., which discloses a container for storing liquid medicaments. The medicaments include an active agent, water and a preservative. The liquid medicament can be insulin containing water and m-cresol, phenol and benzyl alcohol. The container is made from a crystalline polymer of linear or branched olefinic materials obtained from monomers of ethylene, propylene, butylene, or mixtures thereof and having a crystallinity above 35% by weight. The polymeric container is disclosed as providing a barrier against m-cresol, phenol, benzyl alcohol and water.

U.S. Pat. No. 7,029,752 to Hama et al. discloses a plastic container for a liquid medicine to prevent mixing with oxygen and water. The plastic container is made of a plastic material coated with a diamond-like carbon film having a water vapor permeability of 0-0.006 g/container/day and an oxygen permeability of 0-0.011 ml/container/day. The properties are obtained by optimizing the composition, density and film thickness of the diamond-like carbon film.

Many delivery devices such as prefilled syringes, infusion sets and infusion containers have been proposed which have generally been suitable for their intended use. These devices often require a separate storage vessel or ampule to prevent extended contact with the components of the delivery device that can result in degradation of the medicament by extended contact. Therefore, there is a continuing need for improved materials for delivery devices that provide improved storage properties of the medicament.

SUMMARY OF THE INVENTION

The present invention is directed to a storage chamber and/or container for a dispensing or delivery device for a pharmaceutical agent, medicament or liquid medication and to a method for reducing loss of the pharmaceutical agent, medicament or liquid medication during storage. The invention is particularly directed to a dispensing device having a storage vessel, container or chamber for providing improved storage properties for a medicament.

Accordingly, one object of the invention is to provide a storage container, storage vessel or storage chamber for use in connection with a dispensing device or delivery device with a reduced loss of the substance contained therein normally caused by the interaction between the storage device and the substance.

One feature of the invention is to provide an improved storage vessel, storage container or storage chamber for a delivery device made from a polymeric material containing an additive that reduces the loss of stabilizing agents from a medicament or pharmaceutical agent.

In one aspect of the invention, a storage container, storage vessel or storage chamber is produced from a polyolefin resin that includes a fatty acid amide additive to inhibit the migration or diffusion of stabilizing agents from a medicament or pharmaceutical agent. The polyolefin can be a polyethylene, polypropylene, copolymers of polyethylene, and copolymers of polypropylene and cyclic olefin copolymer.

The additive combined with the polymeric material is preferably a fatty acid amide that functions as a migration inhibiting agent for stabilizers in the substance, such as a medicament or pharmaceutical agent, without interfering with the operation of the dispensing device. The polymeric material and the additive provide improved storage stability of the medicament or pharmaceutical agent to provide improved shelf life of prefilled dispensing devices and devices that are filled periodically to dispense the substance over a predetermined period of time. In one embodiment, the dispensing device is an infusion pump that contains a supply of the medicament or pharmaceutical agent. The components of the infusion pump that contact the medicament or pharmaceutical agent formed from the polymeric material and the additive so that the infusion pump stores a larger volume of the medicament or pharmaceutical agent with improved storage life and reducing the need for frequent filling. Generally, the components that contact the medicament or pharmaceutical agent are disposable.

The additive for the polyolefin in one embodiment is selected from the group consisting of lauramide, myristamide, palmitamide, stearamide, behenamide, erucamide, montanamide, stearylerucamide, oleylpalmitamide, methylenebis (stearamide), ethylenebis (myristamide), ethylenebis (palmitamide) and ethylenebis (stearamide). The additive is incorporated into the polyolefin in an amount effective to provide a stabilizing affect for preservatives and stabilizing agents contained in the medicament or pharmaceutical agent. The preferred additives also provide an additional benefit of providing a lubricant surface for the moving parts such as a plunger for a syringe or pump.

Another feature of the invention provides a contact surface for components of a pharmaceutical delivery device that prevents or reduces the loss of stabilizing agents from the pharmaceutical agent. The contact surface can be formed by a layer of a polymeric material containing an additive for inhibiting the loss of the stabilizing agent or preservative. The contact layer can be formed by coextrusion or over molding processes. In other embodiments, the surface of the polymeric material can be coated with the additive and treated to bind the additive to the surface.

One feature of the invention is to provide a method for preventing or inhibiting the loss of stabilizing agents or preservatives from pharmaceutical agents during storage by storing the pharmaceutical agent in a storage container having a contact surface that prevents or inhibits interaction with the pharmaceutical agent. The storage container is made from polyolefin and stabilizing additive. The additive reduces the migration or diffusion of compounds in the pharmaceutical agent into the polymeric material. Reducing the loss of compounds and particularly the preservatives and/or stabilizing agents from the pharmaceutical agent provides improved storage life of the pharmaceutical agent and reduces the need for repeated filling of the delivery device.

The invention is further directed to a method of reducing and inhibiting the loss of preservatives during storage of a pharmaceutical agent or medication such as insulin in a delivery device. The method is particularly suitable for inhibiting the loss of m-cresol, phenol and/or other stabilizing agents from the insulin during storage by reducing the absorption/adsorption of m-cresol and/or phenol into the polymeric material.

The method of the invention provides an extended shelf life of a pharmaceutical agent such as insulin without the need to coat the contact surfaces with a metallized film or provide stainless steel components that are in continuous contact with the pharmaceutical agent.

The various features of the invention are attained by providing a storage chamber for a pharmaceutical agent. The storage chamber comprises a storage container formed from a polyolefin, including a fatty acid amide dispersed in the polyolefin, and a pharmaceutical agent in the storage container and containing a phenolic stabilizing agent in an amount effective to stabilize the pharmaceutical agent. The fatty acid amide is included in the polyolefin in an amount effective to inhibit migration of the fatty acid amide from the pharmaceutical agent into the polyolefin.

The features and advantages of the invention are also attained by providing a method of preserving a pharmaceutical agent comprising the step of containing and storing the pharmaceutical agent in a containment vessel formed of a polyolefin including a fatty acid amide. The pharmaceutical agent includes a phenolic stabilizing agent in an amount effective to stabilize the pharmaceutical agent for prolonged storage. The polyolefin includes the fatty acid amide in an amount effective to inhibit migration of the stabilizing agent from the pharmaceutical agent into the polyolefin.

The features of the invention are further attained by providing a method of inhibiting loss of a stabilizing agent from a pharmaceutical agent during storage. The method comprises the steps of introducing the pharmaceutical agent into and storing the pharmaceutical agent in a storage chamber formed from a polyolefin containing a fatty acid amide. The pharmaceutical agent includes a phenolic stabilizing agent in an amount effective to stabilize the pharmaceutical agent. The fatty acid amide is incorporated in the polyolefin in an amount effective to inhibit migration of the stabilizing agent from the pharmaceutical agent into the polyolefin.

The features of the invention are still further attained by providing a method of inhibiting loss of a phenolic stabilizing agent in an insulin composition during prolonged storage. The method comprises storing the insulin in a containment vessel formed from a polyolefin having an effective amount of a fatty acid amide to inhibit loss of the stabilizing agent from the insulin and degradation of the insulin.

These and other advantages, aspects and features of the invention will become apparent from the following detailed description of the invention, which disclose various embodiments of the invention.

BRIEF DESCRIPTION OF THE DRAWINGS

The following is a brief description of the drawings in which:

FIG. 1 is an explode view of the delivery device in one embodiment of the invention:

FIG. 2 is a cross sectional view of the tube in the embodiment of FIG. 1;

FIG. 3 is an elevational view of the delivery pump in a second embodiment of the invention;

FIG. 4 is a cross sectional view of the supply tube of the embodiment of FIG. 3;

DETAILED DESCRIPTION OF THE INVENTION

Figure 5:
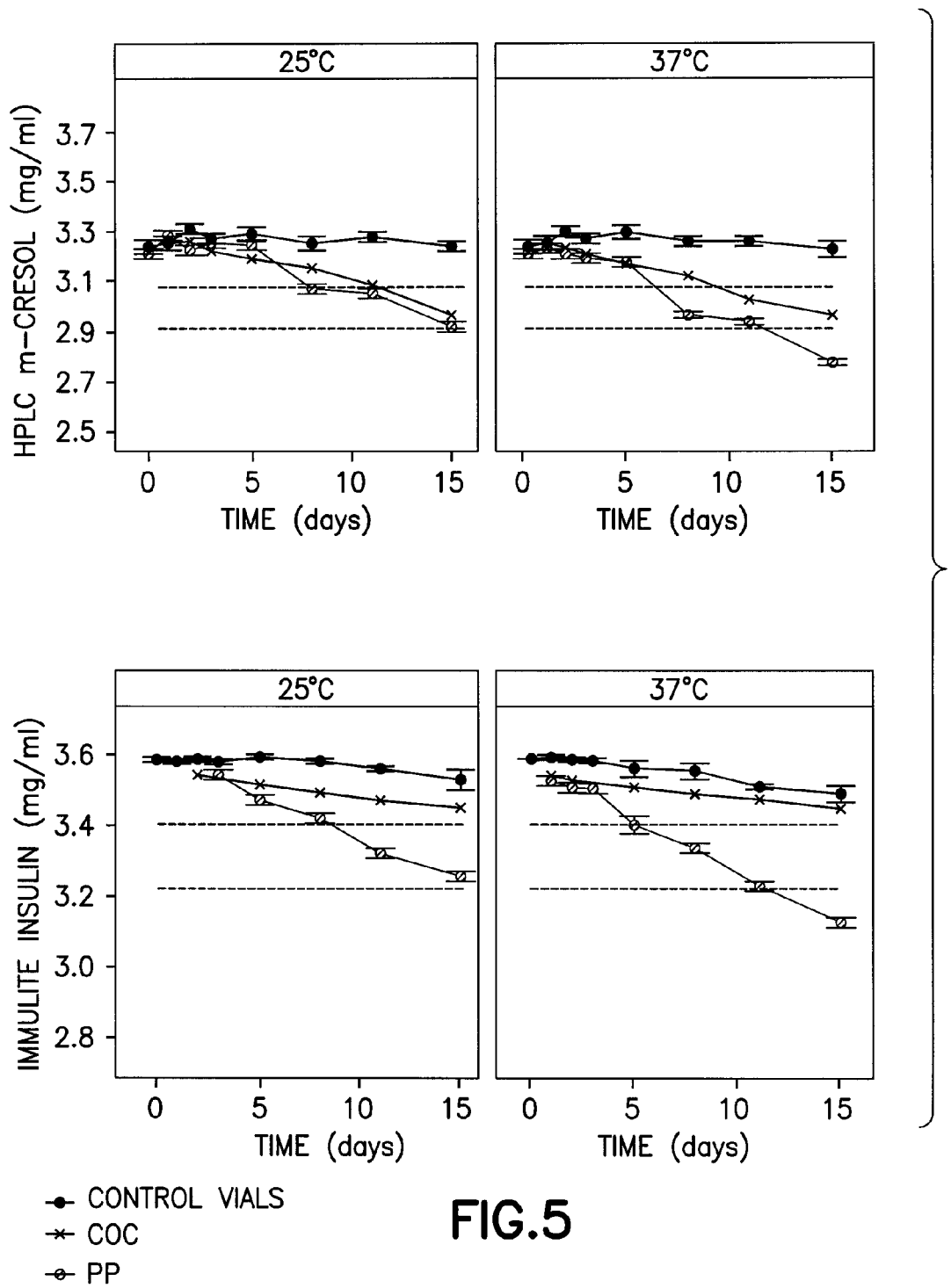
FIG. 5 is a graph of the test results of the experiment of Example 1.

The present invention is directed to a reservoir, storage container, vessel or chamber of a medical device and to a method for reducing loss of a liquid medication, medicament or pharmaceutical agent contained therein. The invention is particularly directed to a reservoir, storage chamber or container and a method for reducing the loss of stabilizing agents from the liquid medication or pharmaceutical agent. In one embodiment of the invention, the medical device is a drug delivery device for delivering the contents of the device at a controlled rate.

The method and device of the invention are suitable for storing, transporting, and the delivery of a liquid medication or pharmaceutical agent that contains a preservative and/or stabilizing agent. The method and device of the invention reduce or inhibit the rate of the loss or migration of the stabilizing agents or preservatives from the medication into or on to the surface of the device.

The method and device are suitable for use with various liquid medications and pharmaceutical agents that require or benefit from stabilizing agents and/or preservatives that can be adsorbed by contact with the surfaces of polymeric materials commonly used to form medical devices. As used herein, the term liquid medication refers to medicaments, pharmaceutical agents, compound and compositions that are administered to a patient and contain an active substance or compound for treating the patient and particularly a human patient.

In one preferred embodiment the liquid medication is insulin for administering to a patient. Insulin commonly requires a stabilizing agent and/or preservative to prevent denaturization of the proteins and the formation of oligomers in order to extend the shelf life of the insulin under different storage temperature and light conditions within the container. Insulin is often stored in glass vials that do not interact with the proteins during storage. The insulin preservatives are often phenolic compounds, such as benzyl alcohol, m-cresol and phenol and mixtures thereof. In other embodiments, the liquid medication can be heparin or other protein based medications. The preferred preservatives are m-cresol, phenol and mixtures thereof with the preferred medication being insulin. The phenolic preservatives are preferably included in the insulin in an amount of about 0.1 mg to about 5 mg per ml of the medication. The m-cresol in insulin acts as a protein conformation stabilizing agent and a preservative.

Preservatives in insulin such as m-cresol, phenol and mixtures thereof have been found to diffuse into polymers such as olefin polymers when the medication is in contact with the surface for prolonged periods of time. It has been found that insulin stored in conventional polymeric containers exhibit loss of m-cresol and phenol which result in polymerization and denaturization of the proteins in the insulin and reduction of the shelf life.

The device of the invention can be any suitable medical device, container, reservoir, vessel or chamber for containing a liquid medication and particularly insulin. Preferably the medical device is a disposable medical device for delivering insulin such as catheter tubing, syringes, pre-filled syringes, insulin cartridges, insulin pumps, patches and other insulin delivery devices. The device of the invention can be any suitable container capable of receiving a supply of the liquid medication for feeding to a delivery device.

In preferred embodiments of the invention the medical device is for "fill-at the time of use" (FTU) devices, such as syringes, reservoirs or containers for delivery devices. The medical device is suitable for devices that are intended to contain a supply of the liquid medication for 1-10 days with reduced loss of the active substance or stabilizing agent in the device when stored at ambient temperature of about 25° C. or elevated temperature at about 37° C. The medical device can be an electro-mechanical, non-disposable insulin pump, insulin reservoirs for disposable or partially disposable patches and pump systems, insulin syringes, insulin pen type cartridges and the like.

The method of inhibiting the loss of preservatives and stabilizing agents from insulin utilize a reservoir, chamber or storage area and/or supply passages, conduits, flexible tubing and the like made from a polymeric material having an additive dispersed therein in amounts to reduce or inhibit the migration and loss of the stabilizing agent into the polymeric material. The storage area or reservoir can be a syringe type reservoir for use in an electro-mechanical pump, reservoir for disposable patches, disposable pump systems, insulin syringes and insulin pen type cartridges. The primary flow path with the delivery device that typically contains the insulin prior to delivery for several days is preferably made for the polymeric material and the additive to inhibit the loss or adsorption of the stabilizing agent and preservatives from the insulin.

One example of a suitable insulin delivery medical device is a pen type device shown in FIG. 1. The delivery device 10 includes a cartridge 12 for a liquid medication such as insulin. Cartridge 12 has a tubular body 14 with an internal cavity for the insulin, a first end 16 and a second end 18. Cartridge 12 is received within the barrel 20 of a housing 22. A needle mounting collar 24 is attached to the discharge outlet end 26 of housing 22. A piercable septum 28 is coupled to the end of cartridge 12 to be pierced by a needle 30. Cartridge 12 is closed by an elastomeric or rubber stopper 32 that provides a fluid tight seal and can slide along the axial length of the cartridge 12 to dispense the contents of cartridge 12.

A dosing device 34 is coupled to the end of housing 22 for actuating the stopper and dispensing the contents of the cartridge 12. Dosing device 34 has a substantially cylindrical shape with a threaded end 36 for connecting to a threaded end 38 of housing 22. A plunger rod 40 extends from the end of dosing device 34 to engage the stopper of the cartridge 12. The dosing device 34 includes a suitable mechanism as known in the art for delivering a selected dosage. The mechanism drives the plunger a selected distance to move the stopper to inject a controlled amount of the medication from the cartridge to the patient.

According to one preferred embodiment of the invention, the cartridge containing the insulin is made from a polyolefin having and additive in an amount effective to inhibit or reduce the loss of m-cresol and/or phenol or other stabilizing agents and preservatives from insulin during storage while contained within the reservoir. The cartridge can be molded by injection molding, blow molding, injection-blow molding or other known molding methods.

The polyolefin is obtained from an unsaturated monomer as known in the art. The polyolefin is preferable a polyethylene, polypropylene, cyclic olefin copolymer, copolymers of polypropylene, and copolymers of polyethylene. One suitable polypropylene is available under the trade name Purell RP 373R from Lyondell Basell Industries. Other suitable polymers and polymer blends include polyurethanes, polyesters, polylactates and copolymers thereof.

The polyolefin is blended with the additive and resulting blend is molded to the desired shaped article or medical device and dimension. The additive is a fatty acid amide selected from the group consisting of lauramide, myristamide, palmitamide, stearamide, behenamide, erucamide, montanamide, stearylerucamide, oleylpalmitamide, methylenebis (stearamide), ethylenebis (myristamide), ethylenebis (palmitamide), ethylenebis (stearamide) and mixtures thereof. Erucamide is a preferred fatty acid amide. The fatty acid amide can be dispersed in the polyolefin in an amount of 0.02 to 2.0 wt % and typically in an amount of about 0.02 to 0.4 wt %. Although not completely understood, it is believed that the fatty acid amide acts as a barrier at the liquid/plastic interface and inhibits the phenolic preservatives from being adsorbed into the polymer at the surface.

The polyolefin is preferable transparent to allow visual inspection of the medication. The polyolefin further has good barrier properties against water; good barrier properties against gasses such as oxygen and carbon dioxide, resistance to environmental stress cracking, good sealing properties and maintain its shape during storage.

The reservoir of the delivery device can also be made from a suitable polymeric resin where the contact surfaces are coated with a polyolefin resin 42 having the fatty acid amide dispersed therein as shown in FIG. 2. The coating can be formed by co-extrusion, over-molding, applied as a solution and fixed to the surface by suitable means such as radio frequency or plasma treatment or other known coating methods. In other embodiments the fatty acid amide can be applied directly to the contact surface and fixed by suitable means. The polyolefin and fatty acid amide blend is particularly suitable for use as a coating for flexible components of an insulin delivery device such a collapsible bladder or diaphragm and/or delivery tube and has a contact surface formed by an inner layer or coating of the polyolefin containing the fatty acid amide.

As shown in the embodiment of FIGS. 3 and 4, an insulin delivery device 50 includes a flexible reservoir tube 52 for use with a roller pump 54. A feed tube 56 having a cannula 58 is connected to the pump delivery system for supplying insulin to the patient. The reservoir tube and the delivery tube are intended for containing a supply of the insulin for several days. In the embodiment shown the reservoir tube and the supply tube are made from a flexible polymeric material with an inner layer 60 forming a barrier to the preservative and stabilizing agents for the insulin as shown in FIG. 4.

The contact surface and flow paths of the insulin are preferably made of the polyolefin containing the fatty acid amide or with a barrier layer formed from the fatty acid amide or blend of the polymer with the fatty acid amide to provide extended storage times for the insulin with reduced loss of m-cresol and/or phenol from the insulin. The fatty acid amide has been found to significantly reduce the migration of m-cresol and other phenolic preservatives in insulin into the polymeric material.

The insulin of the invention refers to insulin from any species such as porcine insulin, bovine insulin, human insulin, and salts thereof. Suitable salts include zinc salts and protamine salts. Other forms of insulin can be active derivatives of insulin and insulin and insulin analogues as known in the art.

Another advantage of the invention is to provide a method for screening and selecting materials for optimum insulin stability. The method establishes a critical minimum level of cresol or other stabilizing agent required to prevent insulin agglomeration into higher molecular weight oligomers. The additive is screened for the rate of preservative loss under various storage and usage conditions by analytical assays such as RP-HPLC, gas chromatography and the like. The derived rate constants can be used to select the appropriate polymeric material and configuration for the reservoir that will provide sufficient stability under the expected conditions of use. The method can be used to select appropriate polymeric materials based on the rate of permeation and preservative stability.

An advantage of the present invention is to provide enhanced insulin stability and reduced m-cresol and phenol adsorption. Insulin pump reservoirs generally store insulin supplies for 1-7 days and pen type injectors store insulin for 30 days such that reduction in the preservative can result in the formation of high molecular weight oligomers. This can result in irritation, redness, swelling, scarring, tissue lipodystrophy and increased levels of anti-insulin antibodies.

Other additives that can be used alone or in combination with the polymers include compounds that can form crosslinks with each other and compounds that can interact with the surface of the polymers. Examples include siloxanes, hydrocarbon chins having at least one reactive site and polyethyleneglycols.

EXAMPLE 1

This example was conducted to determine the loss of preservatives from insulin and to determine insulin stability during storage.

Syringes made from polypropylene under the trade name PH712 and a cyclic olefin copolymer under the trade name Crystal Clear Polymer (CCP) from Becton Dickinson and Company were filled with insulin containing m-cresol and phenol in an amount of about 3.3 mg/ml. The syringes were stored at 25° C. and 37° C. Glass vials were used as the control for insulin stored under the same conditions. The m-cresol levels were measured using HPLC and the insulin levels were measured by Immulite analysis. The graphs of FIG. 5 show the control glass vials exhibit minimal loss of m-cresol and insulin degradation over a 15 day period at 25° C. and 37° C. The graph also shows a loss of m-cresol at 25° C. to about 3.0 mg/ml for the polypropylene syringes and the cyclic olefin copolymer syringes. The polypropylene at 25° C. exhibited a loss of insulin from about 3.6 mg/ml to about 3.1 mg/ml. The cyclic olefin copolymer exhibited a loss of insulin from about 3.6 mg/ml to about 3.4 mg/ml at 25° C. over 15 days and a loss of insulin to about 3.4 mg/ml over 15 days at 37° C.

EXAMPLE 2

Figure 6:
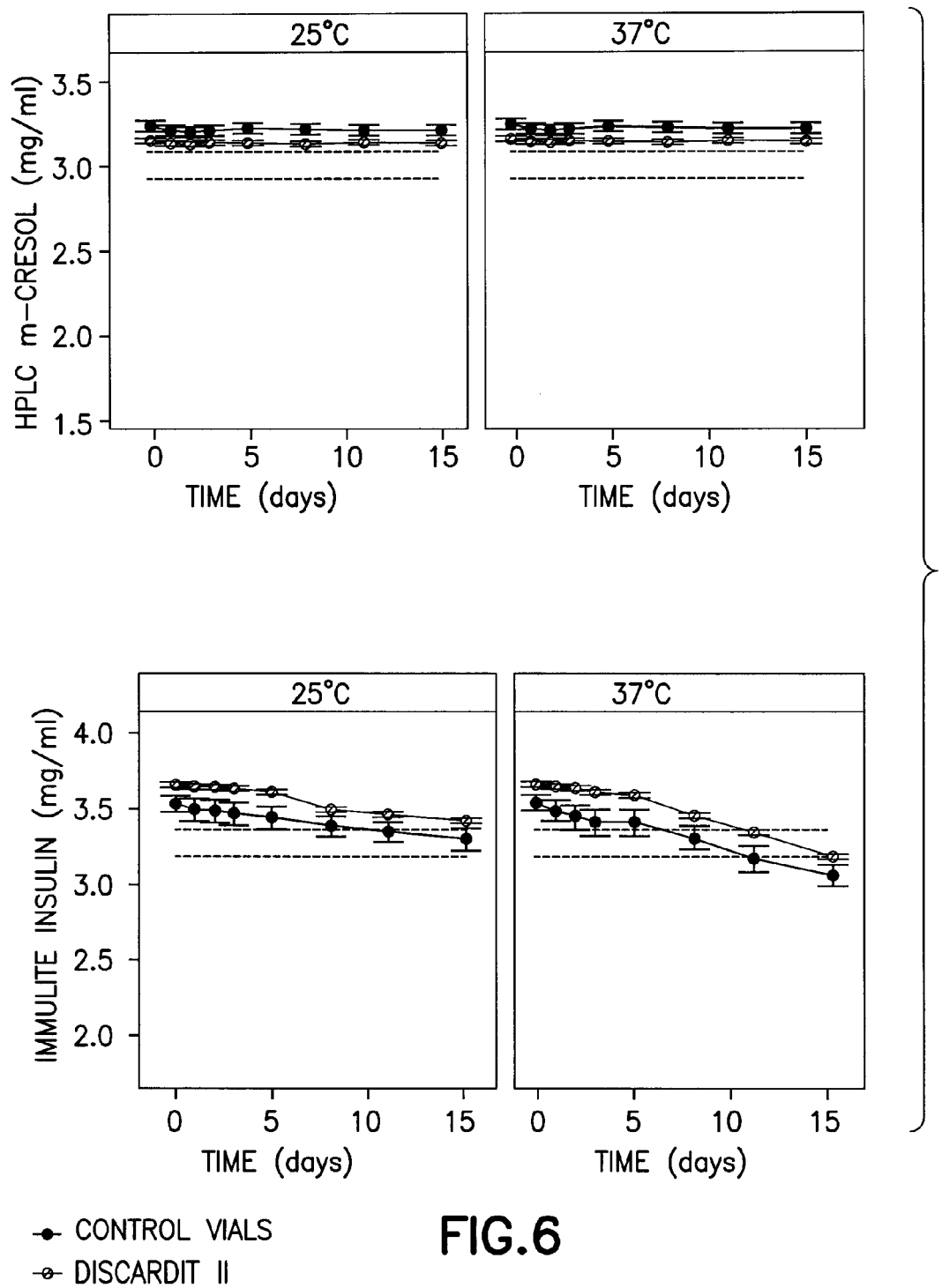
FIG. 6 is a graph of the test results of the experiment of Example 2.

Syringes under the trademark DISCARDIT II made from a cyclic olefin copolymer and erucamide from Becton Dickinson and Company were filled with insulin containing a mixture of m-cresol and phenol were stored at 25° C. and 37° C. Glass vials containing insulin, m-cresol and phenol were stored under the same conditions as a control. The loss of m-cresol was determined by HPLC and the loss of insulin was determined by Immulite analysis. The results are shown in the graphs of FIG. 6. As shown in FIG. 6, the cyclic olefin copolymer at 25° C. and 37° C. showed substantially no loss of m-cresol over a period of 15 days. The loss of insulin at 25° C. and 37° C. were about the same over a period of 15 days.

The test results of these examples demonstrate that the erucamide inhibited the loss of m-cresol and reduce loss of insulin during storage compared to plastic storage containers that do not contain erucamide or other fatty acid amide.

While various embodiments have been chosen to illustrate the invention, it will be understood that various changes and modifications can be made without departing from the scope of the invention as defined in the claims.

What is claimed is:

1. A storage apparatus for a pharmaceutical agent, said storage apparatus comprising:
    a storage container formed from a polyolefin, including a fatty acid amide dispersed in said polyolefin; and
    a pharmaceutical agent in said storage container and containing a phenolic stabilizing agent in an amount effective to stabilize said pharmaceutical agent;
    said fatty acid amide being included in said polyolefin in an amount effective to reduce a rate of migration of said phenolic stabilizing agent from said pharmaceutical agent into said polyolefin.

2. The storage apparatus of claim 1, wherein
    said storage container is a prefilled syringe.

3. The storage apparatus of claim 1, wherein
    said storage container is a storage reservoir of an electromechanical infusion pump assembly.

4. The storage apparatus of claim 1, wherein
    said storage container includes an outer layer and an inner layer, said inner layer being formed from said polyolefin containing said fatty acid amide.

5. The storage apparatus of claim 4, wherein
    said container is flexible tubing.

6. The storage apparatus of claim 4, wherein
    said container is a primary insulin reservoir of an insulin infusion device and where said pharmaceutical agent is insulin.

7. The storage apparatus of claim 1, wherein
    said polyolefin is polypropylene and said fatty acid amide is erucamide.

8. The storage apparatus of claim 1, wherein
    said polyolefin is selected from the group consisting of polypropylene, polyethylene and polypropylene/polyethylene blends.

9. The storage apparatus of claim 1, wherein
said polyolefin is a cyclic olefin copolymer.

10. The storage apparatus of claim 1, wherein
said fatty acid amide is selected from the group consisting of lauramide, myristamide, palmitamide, stearamide, behenamide, erucamide, montanamide, stearylerucamide, oleylpalmitamide, methylenebis(stearamide), ethylenebis(myristamide), ethylenebis(palmitamide) and ethylenebis(stearamide);
and where said stabilizing agent is m-cresol, phenol, or mixtures thereof.

11. A method of preserving a pharmaceutical agent comprising the step of:
containing and storing the pharmaceutical agent in a containment vessel formed of a polyolefin including a fatty acid amide, said pharmaceutical agent including a phenolic stabilizing agent in an amount effective to stabilize said pharmaceutical agent for prolonged storage, and said polyolefin includes said fatty acid amide in an amount effective to reduce the rate of migration of said stabilizing agent from said pharmaceutical agent into said polyolefin.

12. The method of claim 11, wherein
said pharmaceutical agent is insulin and said stabilizing agent is selected from the group consisting of m-cresol, phenol, and mixtures thereof.

13. The method of claim 11, wherein
said fatty acid amide is selected from the group consisting of lauramide, myristamide, palmitamide, stearamide, behenamide, erucamide, montanamide, stearylerucamide, oleylpalmitamide, methylenebis(stearamide), ethylenebis(myristamide), ethylenebis(palmitamide) and ethylenebis(stearamide).

14. The method of claim 11, wherein
said containment vessel is a reservoir of an electro-mechanical infusion pump.

15. The method of claim 14, wherein
said electro-mechanical infusion pump includes flexible tubing made from said polyolefin and fatty acid amide.

16. The method of claim 11, wherein
said containment vessel is a pre-filled syringe containing insulin.

17. The method of claim 11, wherein
said polyolefin is selected from the group consisting of polypropylene, ethylene and polypropylene/polyethylene blends.

18. The method of claim 11, wherein
said polyolefin is a cyclic olefin copolymer.

19. A method of inhibiting loss of a stabilizing agent from a pharmaceutical agent during storage, said method comprising the steps of:
introducing the pharmaceutical agent into and storing the pharmaceutical agent in a storage chamber formed from a polyolefin containing a fatty acid amide, said pharmaceutical agent including a phenolic stabilizing agent in an amount effective to stabilize said pharmaceutical agent, and said fatty acid amide is incorporated in said polyolefin in an amount effective to reduce the rate of migration of said stabilizing agent from said pharmaceutical agent into said polyolefin.

20. The method of claim 19, wherein
said pharmaceutical agent is insulin and said stabilizing agent is selected from the group consisting of m-cresol, phenol, and mixtures thereof.

21. The method of claim 20, wherein
said fatty acid amide is selected from the group consisting of lauramide, myristamide, palmitamide, stearamide, behenamide, erucamide, montanamide, stearylerucamide, oleylpalmitamide, methylenebis(stearamide), ethylenebis(myristamide), ethylenebis(palmitamide) and ethylenebis(stearamide).

22. The method of claim 19, wherein
said storage chamber is an electro-mechanical infusion device.

23. The method of claim 19, wherein
said storage chamber is a flexible tubing of said electro-mechanical infusion device.

24. The method of claim 23, wherein
said flexible tubing has an outer layer and an inner barrier layer in contact with said pharmaceutical agent, said inner barrier layer being formed from said polyolefin and fatty acid amide.

25. The method of claim 19, wherein
said pharmaceutical agent is insulin, said stabilizing agent is selected from the group consisting of m-cresol, phenol, and mixtures thereof, and said fatty acid amide is erucamide.

26. The storage apparatus of claim 1, wherein
said fatty acid amide is included in said polyolefin in an amount of 0.02 to 2.0 wt %.

27. The storage apparatus of claim 1, wherein
said fatty acid amide is included in said polyolefin in an amount of 0.02 to 0.4 wt %.

28. The method of claim 19, further comprising
adding said fatty acid amide to said polyolefin in an amount of 0.02 to 2.0 wt %.

29. The method of claim 19, further comprising
adding said fatty acid amide to said polyolefin in an amount of 0.02 to 0.4 wt %.

30. An insulin delivery device, comprising
a cartridge having an internal cavity and a plunger, said cartridge being formed from a polyolefin and a fatty acid amide, said fatty acid amide selected from the group consisting of lauramide, myristamide, palmitamide, stearamide, behenamide, erucamide, montanamide, stearylerucamide, oleylpalmitamide, methylenebis(stearamide), ethylenebis(myristamide), ethylenebis(palmitamide) and ethylenebis(stearamide); and
an amount of insulin contained in said cartridge, said insulin containing a stabilizing agent selected from the group consisting of m-cresol, phenol, and mixtures thereof, said stabilizing agent being included in an amount effective to stabilize said insulin during storage;
said fatty acid amide being included in said polyolefin in an amount effective to inhibit migration of said stabilizing agent from said insulin into said polyolefin.

* * * * *